Figure 1:
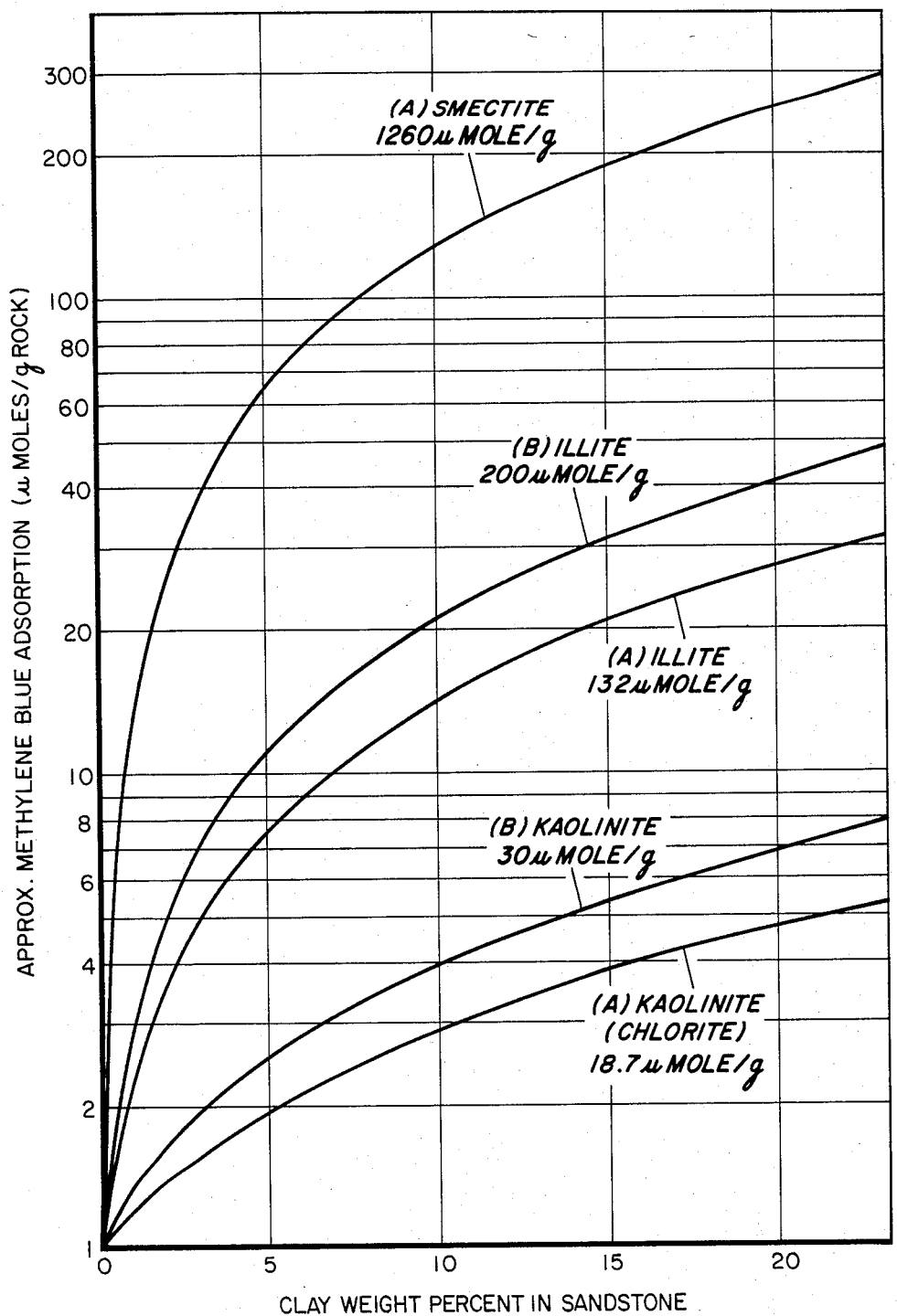

United States Patent [19]

Siebert et al.

[11] Patent Number: 4,495,292

[45] Date of Patent: Jan. 22, 1985

[54] DETERMINATION OF EXPANDABLE CLAY MINERALS AT WELL SITES

[75] Inventors: Robert M. Siebert; Richard W. Lahann, both of Ponca City, Okla.

[73] Assignee: Conoco Inc., Ponca City, Okla.

[21] Appl. No.: 418,852

[22] Filed: Sep. 16, 1982

[51] Int. Cl.$^3$ .................. G01N 31/06; G01N 33/24
[52] U.S. Cl. ........................................ 436/25; 436/31; 436/72; 73/61 R; 73/153; 175/50
[58] Field of Search ................ 436/29, 30, 31, 72, 436/75, 164, 25; 166/250; 175/50; 73/152, 153, 61 R

[56] References Cited

U.S. PATENT DOCUMENTS 3,607,078 9/1971 Dietert et al. ..................... 436/72

OTHER PUBLICATIONS

"Determination of Cation Exchange Capacity by Methylene Blue Adsorption", Nevins et al., Ceramic Bulletin, vol. 46, No. 6, 1967, pp. 587–592.
Journal of Sedimentary Petrology, vol. 37, No. 4, pp. 1221–1230, Dec. 1967, Roy K. Taylor.
Standard Methods for Testing Molding Sands, published by American Foundrymen's Society.
British Clayworker, vol. 77, No. 916, pp. 32–34, 1968, "Simple Test for Clay Identification", Ramachandran, V. S. and Ahmad, F. V.

Primary Examiner—Barry S. Richman
Assistant Examiner—Joseph P. Carrier
Attorney, Agent, or Firm—Cortlan R. Schupbach

[57] ABSTRACT

A dye adsorption procedure for determining clay type and amount in subterranean formation. The procedure can be carried out at a well-site, providing rapid, accurate information for treatment of the well penetrating the formation.

5 Claims, 2 Drawing Figures

DETERMINATION OF EXPANDABLE CLAY MINERALS AT WELL SITES

This invention relates to drilling wells and particularly to a method of determining the water sensitivity of clay materials in earth formations penetrated by the drilled well. Determination is rapidly and accurately made at the well site, eliminating extensive, costly, and time consuming laboratory techniques.

During the calculation of potential production of natural petroleum containing formations, petroleum engineers need to know the proportion of various minerals in the subterranean formations in order to maximize oil and gas production. In making such a calculation, it is necessary to know not only the total porosity and permeability of sand or shale formations comprising the petroliferous reservoir, but also the propensity of such formations to absorb and maintain water when a water differing from the original formation water is introduced during drilling, fracturing or production.

It has long been known that certain types of clays in petroleum reservoirs affect well logging response due to water absorbance. It is necessary, therefore, to obtain an early indication of what types of clay are present in petroliferous reservoirs such that subsequent drilling, testing, completion and production practices may be designed to reduce or eliminate possible formation damage. If such practices are improperly carried out, a petroliferous formation penetrated by a well bore can be irrevocably damaged such that additional wells must be drilled at great expense of both time and money.

It has long been known that the presence of expandable (or smectitic) clays is particularly troublesome to well completion and production. Also, many illite clays have varying degrees of expandability and thus may also be troublesome (although to a lesser extent than the smectites).

Well site tests for determining properties or conditions of formations being drilled are known as disclosed by U.S. Pat. Nos. 3,670,829; 3,722,606; 3,766,993; and 3,921,732.

These patents all deal with methods of detecting pressure conditions in well bores by utilizing samples of shale from the well bore. U.S. Pat. No. 2,207,348 relates to a method of drilling wells and determining the connate water content of earth formations penetrated by the wells. This method utilizes reducing sugars in drilling mud.

However, to date the only reliable method of determining the type of clays in formations penetrated by a well bore has been the costly and very time consuming X-ray diffraction method for clay analysis. In general, the X-ray diffraction analysis requires an aliquot of the sample which is crushed and ground to a very fine particle size. The rock powder is then edge-packed in a shallow plastic dish so as to create a random particle distribution which is then analyzed by standard X-ray diffraction procedures. The resulting X-ray diffraction pattern is compared to patterns obtained from known materials. Relative peak heights are measured and a composition by mineral is calculated. When all phases are identified, the composition is normalized to 100%. Thus the random powder diffraction pattern yields at best an estimate for total clay. Identification of various clay types within the formation then proceeds by preparation of an oriented amount of 4 micrometer particles. The steps involved in X-ray analysis of these particles are long, complex and involve multiple washing steps as well as multiple heating steps for each sample.

It would therefore be of great benefit to provide an accurate, rapid method for determining the type of and approximate amount of clay minerals in petroliferous formations penetrated by a well bore. Preferably the method should be sufficiently simple to be carried out at the well site so that an accurate and rapid determination can be made, decisions made thereupon and action implemented as soon as possible.

It is therefore an object of the present invention to provide a rapid method for the determination of type and approximate amount of clay minerals in subterranean formations. Other objects will become apparent to those skilled in this art as the description proceeds.

We have now discovered that the type and approximate amounts of clay in subterranean formations can be determined utilizing a procedure comprising (1) sampling the formation and weighing the sample;

(2) crushing and waterwashing the sample, and (3) adding the sample to an organic dye aliquot having a known concentration, thereby forming a solid phase and a liquid phase, and then (4) measuring optical adsorption of the liquid phase to determine the amount of organic dye remaining in the phase, wherein the amount of organic dye adsorbed on the sample is directly proportional to the surface area of clay in the formation.

In general, subterranean formations containing sandstone likewise contain clays of various types. Among the clays are kaolinite, which generally poses no problem during well completion and production since it is not water sensitive. However, illite type clays have extremely high surface area and tend to block pore networks in a formation and reduce formation permeability when present in amounts above small quantities. Some illites are partly water sensitive and expand when non-formation waters (any water that does not have the same chemical composition and pH as the original formation waters) are introduced, such as when drilling, fracturing or water-flooding a formation is carried out. These well operations cause further blockage of the formation's pore networks, causing further decline in or damage to formation permeability.

An even greater problem is encountered with smectite clays. Smectite clays also block pore networks of formations as do the illites, but because of their high water-sensitivity on expandability, the introduction of non-formation waters can cause severe swelling of the smectite with resultant severe permeability damage.

It is necessary to know the type of clay and relative amounts of each in a formation in order to maximize hydrocarbon production from such formations. Table 1 shows the relative surface areas of sandstone containing varying amounts of these common clays.

TABLE 1

| Sandstone Composition (Weight Percent) | | Calculated Surface Area ($m^2/g$) |
|---|---|---|
| Quartz | Clay | |
| 100 | — | 0.036 |
| 99 | 1 Kaolinite | 0.12 |
| 98 | 2 Kaolinite | 0.21 |
| 95 | 5 Kaolinite | 0.46 |
| 99 | 1 Illite | 0.82 |
| 98 | 2 Illite } v. low | 1.60 |
| 95 | 5 Illite } expandability | 3.93 |
| 99 | 1 Montmorillonite | 7.46 |
| 98 | 2 Montmorillonite } Smectite | 14.89 |

TABLE 1-continued

| Sandstone Composition (Weight Percent) | | Calculated Surface Area (m²/g) |
|---|---|---|
| Quartz | Clay | |
| 95 | 5 Montmorillonite | 37.18 |

The present invention allows a determination of relative amounts of expandable (water-sensitive) clays in formations based upon the differences in dye absorption between heated and unheated samples. The amount of organic dye which can be adsorbed by unit weight of formation samples is determined and this value is used as a measure of approximate quantity of expandable clay. In general, sandstone cuttings with no visible matrix clay give adsorption values equivalent to surface areas greater than about 5 square meters per gram when significant quantities of expandable clays are present. Intermediate values indicate small amount of swelling clays or more significant amounts of kaolinite or illite. Very low absorption indicate the sandstone is low in or essentially free of clay. In table 1, the amount of organic dye which is adsorbed is directly proportional to the surface areas shown. When carrying out the process of the present invention, samples are normally made up of cuttings or core pieces. These samples can be collected at the wall site without difficulty.

In determining the quantity of clays in the formation, representative chips are hand picked from course cuttings fraction, washed and gently dissegregated by crushing. This material is either then used with an original cation exchange population or is sodium saturated with a concentrated sodium chloride solution in order to make the heat treatment of the present invention more effective in determining content of expandable clay. The need for sodium saturation will be determined experimentally. The sample is then split into aliquots. One aliquot is added to a known volume of dye solution having a known concentration and gently agitated for a specific time. The suspended material is spun down in a small centrifuge and the supernatant is analyzed for the concentration of remaining dye. Such analysis can be by visual comparison or by use of a small spectrophotometer. After absorption has been determined, a sample aliquot will be heated to a temperature of from about 400° C. to about 600° C. for a time ranging from about 20 minutes to about 6 hours. Preferably the sample will be treated at about 550° C. for about 30 minutes, whereafter the absorption is redetermined. If absorption after heating is significantly less than before expandable clays are indicated.

In carrying out the process of the present invention, samples are treated with any organic dye capable of adsorption on a silica mineral surface. Representative but non-exhaustive examples of dyes suitable in the present invention are safranine "y", malichite green, methylene blue, magda red, rosaniline, methyl red, methyl violet and crystal violet or analogues of these.

For more precise results the color produced can be compared either with a simple color comparator or more accurately with a small absorption spectrometer. Representative but non-exhaustive examples of such suitable spectrophotometers are Spectronic 20, trademark of and sold by Bausch and Lomb.

An alternative method for determining expandable clay content using the basic dye absorption technique is possible. A dye is selected which adsorbs only on clay exterior surfaces or smectitic inner layer surfaces. The expandable clay content is proportional to the difference in dye adsorption capacity between the new dye and the original dye used.

Another alternative method for determining the expandable clay content using the basic dye adsorption technique utilizes the dye adsorption of the dried sample from a non-polar or low polarity solvent as a measure of the total exterior surface area of the sample. The non-polar solvent does not allow the expandable clays to expand, thereby preventing dye adsorption in the clay inter layer position. The difference between the non-polar solvent adsorption and the adsorption from water (which does allow dye to adsorb in the inter layer positions) is used to calculate the expandable clay content as outlined under the heating technique.

Any dye which is capable of adsorption on silicate mineral surfaces is suitable. The particular solvent used is selected based on the properties of low polarity and appreciable solubility of the dye in the solvent. In the case of methylene blue, representative but non-exhaustive examples of suitable solvents are chloroform, trichloroethane or one of the dichloroethanes.

Methods are known for determining the methylene blue adsorption on surface areas of several clays, as set forth in *Clay Organic Studies, Clay as in Clay Minerals*, volume 18, pages 203 to 212 by Hang and Brindley, 1970. Values set forth in this reference are reproduced in Table 2.

TABLE 2

| | Adsorbed Methylene Blue (meq/100 g) | Methylene Blue Surface Area (m²/g) |
|---|---|---|
| Kaolinite | 1.1 | 8.6 |
| Oswego Illite | 10 | 78 |
| Wyoming Montmorillonite | 95 | 743 |
| Quartz Sand (0.25 mm grain size) (Calculated) | — | 0.036 |

It should be noted that greater than a 20,000 fold increase in surface area is noted when pure quartz sand is compared to pure montmorillonite clay.

Determination of the dye absorption after heating a sample aliquot allows a close estimate to be made of the amount of smectite clays in the sample since the collapsed smectite (after water is removed) absorbs dye at a rate similar to illite after heating. The technique is illustrated in the equations set forth below where mmole/g Rock = micromole per gram of Rock
$\Delta AS$ = Difference in dye adsorption between heated and unheated sample
AS = Total adsorption of sandstone sample (mmole dye)
AR = Adsorption Rate (mmole Dye/g Clay) of a clay
AC = Total adsorption of a clay in the sample $$AS^{unheated} = AC^{smectite}_{heated} + AC^{illite}_{unheated} + AC^{kaolinite/chlorite}_{unheated}$$

$$AS^{heated} = AC^{smectite}_{heated} + AC^{illite}_{heated} + AC^{kaolinite/chlorite}_{heated}$$

$$\Delta AS = AS^{unheated} - AS^{heated}$$

$$= AC^{smectite}_{unheated} - AC^{smectite}_{heated}$$

when $AC^{illite}_{heated} = AC^{illite}_{unheated}$ $$AC^{kaolinite/chlorite}_{heated} = AC^{kaolinite/chlorite}_{unheated}$$

$$\Delta AS = \text{weight smectite} \times AR^{smectite}_{unheated} -$$

$$\text{weight smectite} \times AR^{smectite}_{heated}$$

-continued when $AR^{smectite}_{heated} = AR^{illite}_{unheated}$ then weight smectite = $\dfrac{\Delta AS}{AR^{smectite}_{unheated} - AR^{illite}_{unheated}}$ In identifying the amount of smectite (water sensitive swelling clays) the heating method is definitive in identifying smectites. Samples must be heated for a time and a temperature sufficient to collapse the smectite. This is done by heating the sample to a temperature of from about 400° C. to about 600° C. for periods of time ranging from about 20 minutes to about 6 hours. However, for practical purposes the sample will normally be heated at temperatures of from about 550° C. for about ½ hour. Thus a careful use of temperature is necessary in the present invention.

The very fact that samples have methylene blue absorptions greater than about 30 micromoles per gram of rock indicate clays which are dominated by smectite. Given the sample absorption value in these cases, the weight of smectite can be closely estimated by calculation. The calculated result becomes more accurate as the total absorption value becomes larger. The accuracy of this estimate and the accuracy increased with increasing smectite can be seen from FIG. 1.

In FIG. 1 all "A" curves were calculated using clay adsorption values measured according to the procedure of Hang and Brindley. All "B" curves were determined using clay adsorption values determined by the method of the present invention. The adsorption is the total adsorption of clay-free sandstone plus the adsorption of pure clay.

The total adsorption value for an illite bearing sandstone sample cannot rise above about 40 micromoles per gram of rock or about 7 micromoles per gram of rock for kaolinite bearing rocks. Samples with 20 weight percent or more illite are rare in practice.

Figure 2:
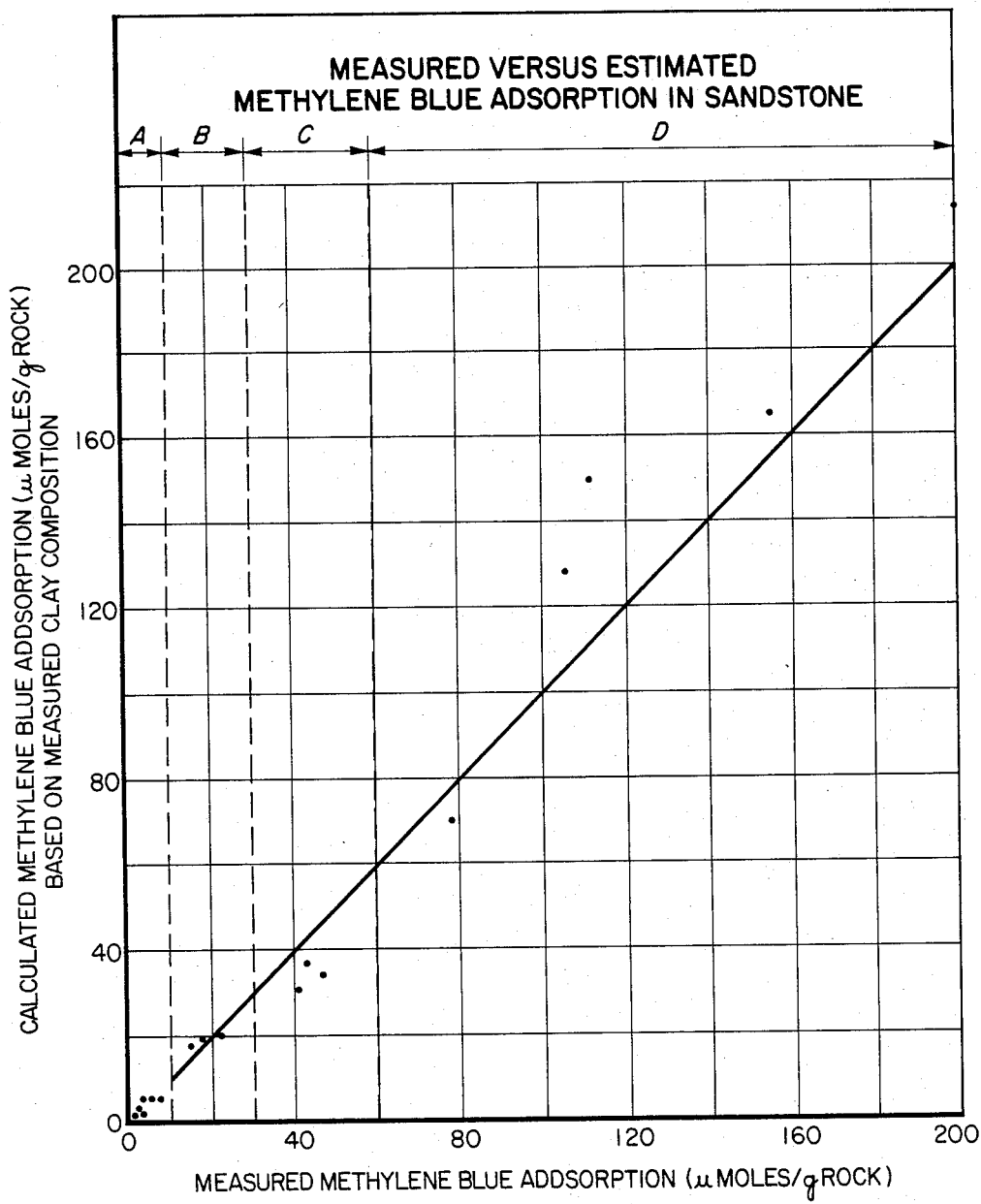

The present invention provides an extremely good measure of water sensitivity in sandstone reservoirs due to the fact that some illite clays have an associated water swelling component. Thus, a sample with an absorption greater than about 10 micromoles per gram of rock would have some degree of water sensitivity (water sensitivity referring to the swelling nature of the clay which can cause permeability damage in formations, when exposed to different waters during the drilling process). Water sensitivity of the present invention is set forth in FIG. 2, which shows measured versus estimated adsorption in some sandstone samples. In the figure, the estimated values were calculated using point count clay volume percentages and the absorption rates of Hang and Brindly (1970). Clay mineral identification was based on X-ray diffraction techniques currently in use. In the figure area A is clean sandstone or kaolinite containing sandstones with very minor amounts of illite of smectite. Area B is sandstones with illite and minor smectite having only minor water sensitivity. Area C is sandstone with water sensitive illite and some smectite. Area D is sandstones with significant extremely water-sensitive smectite. The figure shows an extremely good correlation between the values measured using a method of the present invention and the currently practiced, time-consuming x-ray diffraction. The measured adsorption values for the 17 samples took less than 4 hours to accomplish. The estimated values using X-ray diffraction and thin-section techniques required about 2 weeks.

To determine clay type and general water sensitivity at the well site for one sample would require less than 1½ hour (including heating step) whereas by X-ray diffraction nearly 1½ days would be required for processing and interpretation, not including the shipping time to get the samples to the laboratory.

The invention is more concretely described with reference to the examples below wherein all parts and percentages are by weight unless otherwise specified. The examples are provided to illustrate the present invention and not to limit it.

EXAMPLE 1

Utilizing methylene blue (MB) as the organic dye, sandstone samples were selected from conventional cores or picked from drill cutting samples using a binocular microscope. These samples were grain-supported rocks comprised of grains in the size ranging from 0.01 to 1 millimeter. Samples consisted of about 5 grams of material. The samples were washed free of drilling mud and patted dry with a paper towel.

Approximately 1 gram aliquot of the samples were weighed to ±0.005 grams and gently crushed with a mortar and pestal to completely disaggregate the sand grains. No grinding was carried out. The sample was then quantitatively transferred to a 15 or 20 milliliter centrifuge tube and 10 to 20 milliliters of distilled water or other washing solution was added. After shaking the suspension to wash the sample, the suspended solid was spun down in a small centrifuge and the supernatant decanted. The washing process was repeated.

Exactly 10 milliliters of an aqueous methylene blue solution of appropriate concentration was added to a centrifuge tube. The tube was stoppered and placed on a mixer which was run at a speed sufficient to keep the solid in constant suspension. Appropriate concentrations for the various rock absorbances are set forth in Table 3.

TABLE 3

| Rock Absorbance micro-moles M.B./ gram rock | Methylene Blue Concentration moles/liter |
| --- | --- |
| 0.5 to 5.0 | 0.0005 |
| 5 to 10 | 0.001 |
| 10 to 50 | 0.005 |
| 50 to 200 | 0.02 |

After 30 minutes of agitation, the sample was spun down on the centrifuge for 10 minutes or until no Tyndal effect was observed. The Tyndal effect is the ability of very fine particles and colloids in liquid suspension to scatter light (and thus become visible) from a strong, collimated beam of light. An aliquot of the supernatant was pipetted from the centrifuge tube and diluted to an appropriate concentration range in a volumetric flask for the method of analysis. For the experiments carried out, the spectrometer used was a Bausch and Lomb Spec 20 for which an appropriate concentration range was between $2 \times 10^{-5}$ and $2 \times 10^{-6}$ molar.

Since an instrument utilizing cuvettes was used, a clean cuvette was filled with a diluted solution, placed in the instrument and the transmittance as percent was read. The measurements were taken at 6500 angstrom wavelength. The value of methylene blue in the unknown solution was read from the standard graph of concentration vs transmittance which was produced by measurements of dilutions made from a methylene blue solution of known concentrations. The calibration of the curve was checked by occasionally measuring a standard solution.

The adsorbance of the samples was calculated by

Adsorbance of Rock (mmole M.B./g Rock) =

$$\frac{\text{Concentration of (moles/liter)} \times \text{Dilution Factor} + 1000 \left(\text{liter} \cdot \frac{\mu\text{moles}}{\text{mole}}\right)}{\text{Weight of Sample (grams)}}$$

Results of the samples taken are set forth in Table 4.

TABLE 4

Estimated versus Measured Methylene Blue Adsorption

| Sample | Measured Adsorption μ mole/g Rock | Volume % Clay | Clay Type | Estimated Adsorption μ mole/g Rock |
|---|---|---|---|---|
| 1 | 3.4 | 1.1 | Kaolinite | 5.0 |
|   |     | 2   | Illite    |     |
| 2 | 7.0 | 1.3 | Kaolinite | 5.6 |
|   |     | 2.5 | Illite    |     |
| 3 | 5.6 | 0.9 | Kaolinite | 4.8 |
|   |     | 2   | Illite    |     |
| 4 | 155.7 | 23 | Smectite | 165 |
| 5 | 112.4 | 21 | Smectite | 150 |
| 6 | 22.1 | 25 | Illite | 20 |
| 7 | 16.3 | 22 | Illite | 18 |
| 8 | 47.2 | 75 | Illite | 34 |
|   |      | 25 | Smectite |    |
| 9 | 78.1 | 10 | Smectite | 70 |
| 10 | 1.7 | 0 | — | 1 |
| 11 | 42.8 | 5 | Smectite | 37 |
| 12 | 1.0 | 0 | — | 1 |
| 13 | 2.6 | 0 | — | 1 |
| 14 | 15.8 | 6.4 | Illite | 17.8 |
|    |      | 1.6 | Smectite |     |
| 15 | 19.0 | 7.2 | Smectite | 19.4 |
|    |      | 1.8 |          |     |
| 16 | 106.3 | 18 | Smectite | 128 |
| 17 | 40.3 | 9 | Illite | 31 |
|    |      | 3 | Smectite |    |

In the table, volume percent clay was determined by point count of thin sections. The clay type assumed that chlorite absorbed methylene blue at the kaolinite rate. Estimated absorption was read from the chart of FIG. 1 using volume percent scale and curves based on measurements of pure clays from Hang and Brindley (1970).

EXAMPLE 2

A comparison was made using polar and non-polar solvents in the process of the present invention. Two solutions with identical amounts of methylene blue were made using water and chloroform respectively. These two solutions were titrated with montmorillonite smectite clay until the solution was decolorized. The chloroform solution required 3.5 times by weight more clay than the water solution to decolorize, indicating that the inter layer adsorption sites were blocked in the low polarity solvent.

The basic technique used for determining dye adsorption from aqueous solution can be used for adsorption from non-polar solvents with simple changes in procedure. After the formation sample is crushed, an aliquot is dried by at least 2 washings in pure acetone and then dried under a heat lamp. After the dye absorption and centrifuging of the sample, a fixed volume of the non-polar solvent plus unabsorbed dye is taken and evaporated to dryness. The resulting dye residue is dissolved in a volume of water and analyzed in the normal manner. This procedure avoids the necessity of making analytical standards for the dye in the non-polar solvent. Alternatively, for those dyes with high solubility in water, the residue dye in the non-polar solvent is extracted by shaking with a knowm volume of water. Analysis is then performed on the water phase.

In place of the equipment actually used for the spectrophotometry, other analytical equipment is available. Simple visual color comparator can be used in place of a spectrophotometer with good results. In addition, spectrophotometers are available which use an immersion probe instead of a cuvette which would be very suitable for the practice of the present invention.

While certain embodiments and details have been shown for the purpose of illustrating this invention, it will be apparent to those skilled in this art that various changes and modifications may be made herein without departing from the spirit or scope of the invention.

We claim:

1. A method for determining the expandable clay content of subterranean formations comprising (1) sampling said formations, (2) adding a portion of said sample to a solution of organic dye in a non-polar or low polarity solvent, (3) adding a second portion of said sample to a solvent of organic dye in water or a polar solvent, and determining the expandable clay content as the difference between non-polar solvent adsorption and water or polar solvent adsorption.

2. A method as described in claim 1 wherein the organic dye is selected from the group consisting of methylene blue, rosaniline, malichite green, magda red, methyl violet, crystal violet or methyl red.

3. A method as described in claim 2 wherein the organic dye is methylene blue and the non-polar solvent is selected from the group consisting of chloroform, trichloroethane or a dichloroethane.

4. A method as described in claim 3 wherein a determination of expandable clay content is carried out visually using a precalibrated color chart.

5. A method as described in claim 3 wherein the determination of expandable clay content is carried out by an absorption spectrophotometer.

* * * * *